(12) United States Patent
Kong

(10) Patent No.: US 11,103,748 B1
(45) Date of Patent: Aug. 31, 2021

(54) SYSTEM AND METHOD FOR HUMAN MOTION DETECTION AND TRACKING

(71) Applicant: Physmodo, Inc., Dallas, TX (US)

(72) Inventor: Longbo Kong, Frisco, TX (US)

(73) Assignee: Physmodo, Inc., Dallas, TX (US)

( * ) Notice: Subject to any disclaimer, the term of this patent is extended or adjusted under 35 U.S.C. 154(b) by 0 days.

(21) Appl. No.: 17/260,477

(22) PCT Filed: Mar. 5, 2020

(86) PCT No.: PCT/US2020/021262
§ 371 (c)(1),
(2) Date: Jan. 14, 2021

(87) PCT Pub. No.: WO2020/181136
PCT Pub. Date: Sep. 10, 2020

Related U.S. Application Data

(60) Provisional application No. 62/814,147, filed on Mar. 5, 2019.

(51) Int. Cl.
*H04N 9/47* (2006.01)
*A63B 24/00* (2006.01)
(Continued)

(52) U.S. Cl.
CPC ...... *A63B 24/0003* (2013.01); *A63B 24/0062* (2013.01); *A63B 71/0622* (2013.01);
(Continued)

(58) Field of Classification Search
CPC .... G06T 7/50; G06T 7/60; G06T 7/90; G06T 7/215; G06T 7/285; G06T 19/20;
(Continued)

(56) References Cited

U.S. PATENT DOCUMENTS 7,070,571 B2 7/2006 Kramer et al.
8,876,739 B2 11/2014 Salarian et al.
(Continued)

FOREIGN PATENT DOCUMENTS

CN 102402288 4/2012
CN 105069413 11/2015
WO PCT/US18/12080 1/2018

OTHER PUBLICATIONS

Longbo Kong et al. "A Hybrid Framework for Automatic Joint Detection of Human Poses in Depth Frames," Patterns Recognition vol. 77. May 2018, pp. 216-225.
(Continued)

*Primary Examiner* — Peet Dhillon
(74) *Attorney, Agent, or Firm* — Scott Griggs; Griggs Bergen LLP

(57) ABSTRACT

A system and method for human motion detection and tracking (10) are disclosed. In one embodiment, an optical sensing instrument (16) monitors a stage (24). A memory (182) is accessible to a processor (180) and communicatively coupled to the optical sensing instrument (16). The system (10) captures a depth frame (150) from the optical sensing instrument (16). The depth frame (150) is converted into a designated depth frame format (152), which includes at each image element second coordinate values relative to the depth frame (150). Probability distribution models are applied to the designated depth frame format (152) to identify a respective plurality of body parts. The position of each of the respective plurality of body parts in the designated depth frame format (152) is calculated as is the position of each of the respective plurality of body parts in the depth frame (150).

10 Claims, 10 Drawing Sheets

(51) Int. Cl.
  *G06K 9/00* (2006.01)
  *G06T 7/50* (2017.01)
  *G06T 7/73* (2017.01)
  *G06T 7/246* (2017.01)
  *A63B 71/06* (2006.01)

(52) U.S. Cl.
  CPC .......... *G06K 9/00369* (2013.01); *G06T 7/246* (2017.01); *G06T 7/50* (2017.01); *G06T 7/73* (2017.01); *A63B 2220/05* (2013.01); *A63B 2220/13* (2013.01); *A63B 2220/807* (2013.01); *G06T 2207/10028* (2013.01); *G06T 2207/20081* (2013.01); *G06T 2207/20084* (2013.01); *G06T 2207/30196* (2013.01)

(58) Field of Classification Search
  CPC .. H01L 27/14; G06K 9/78; A61B 5/04; A63B 24/0003
  See application file for complete search history.

(56) References Cited

U.S. PATENT DOCUMENTS

| | | | |
|---|---|---|---|
| 9,149,222 | B1 | 10/2015 | Zets et al. |
| 2008/0212836 | A1 | 9/2008 | Fujimura et al. |
| 2008/0221487 | A1 | 9/2008 | Zohar et al. |
| 2011/0298827 | A1* | 12/2011 | Perez ................. G06K 9/00355 345/647 |
| 2013/0268205 | A1 | 10/2013 | Aragones et al. |
| 2014/0254883 | A1 | 9/2014 | Kim et al. |
| 2014/0276095 | A1 | 9/2014 | Griggs et al. |
| 2014/0348403 | A1* | 11/2014 | Kurtz ..................... G16H 40/67 382/128 |
| 2016/0066838 | A1* | 3/2016 | DeCharms ........... A61B 5/4824 434/236 |
| 2016/0247017 | A1 | 8/2016 | Sareen et al. |
| 2016/0346601 | A1 | 12/2016 | Marcandelli et al. |
| 2017/0086712 | A1 | 3/2017 | Mauro et al. |
| 2018/0164947 | A1 | 6/2018 | Mizuhashi et al. |
| 2018/0189550 | A1 | 7/2018 | McCombe et al. |
| 2018/0336973 | A1* | 11/2018 | Tadi ........................ A61B 5/11 |
| 2019/0012530 | A1* | 1/2019 | Tomono ................. G06K 9/623 |
| 2019/0038181 | A1* | 2/2019 | Domeika ............. A61B 5/7267 |
| 2019/0340671 | A1* | 11/2019 | Tran ................... G06Q 30/0631 |

OTHER PUBLICATIONS

Ankur Agarwal et al. "Recovering 3D human pose from monocular images". IEEE Transactions on Pattern Analysis and Machine Intelligence, Institute of Electrical and Electronics Engineers, 2006, 28 (1), pp. 44-58. ff10.1109/TPAMI.2006.21ff. ffinria-00548619.

Alireza Shafaei et al. "Real-Time Human Motion Capture with Multiple Depth Cameras," 2016 13th Conference on Computer and Robot Vision (CRV), Victoria, BC, 2016, pp. 24-31, doi: 10.1109/CRV.2016.25.

CROSSFIT "The Overhead Squat" video published on Youtube.com on Feb. 25, 2019.

PCT/US20/21262 Notification of Transmittal of the International Search Report and the Written Opinion of the International Searching Authority, or the Declaration filed Mar. 5, 2020.

* cited by examiner

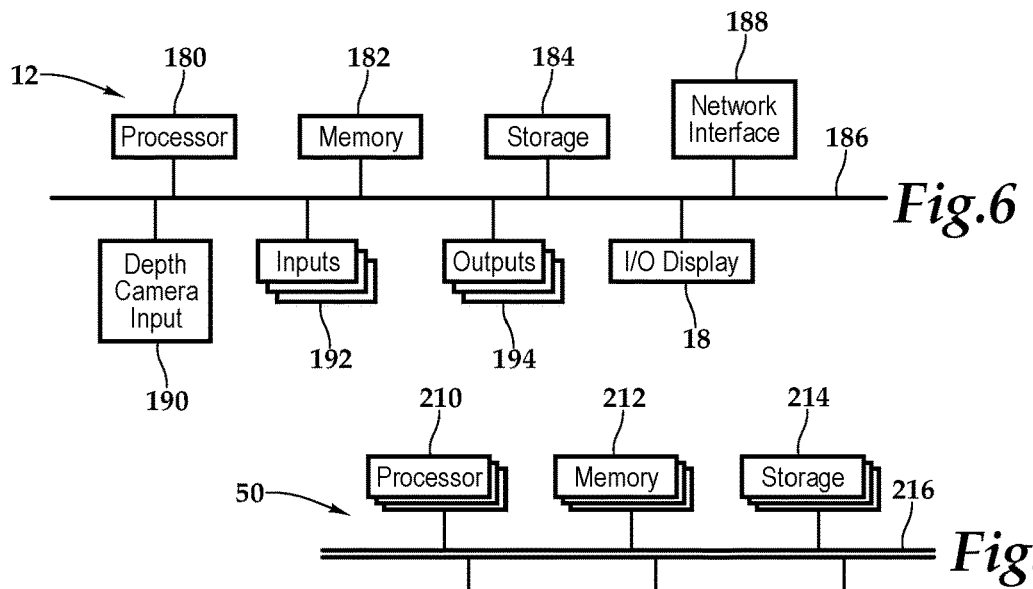
Fig.6
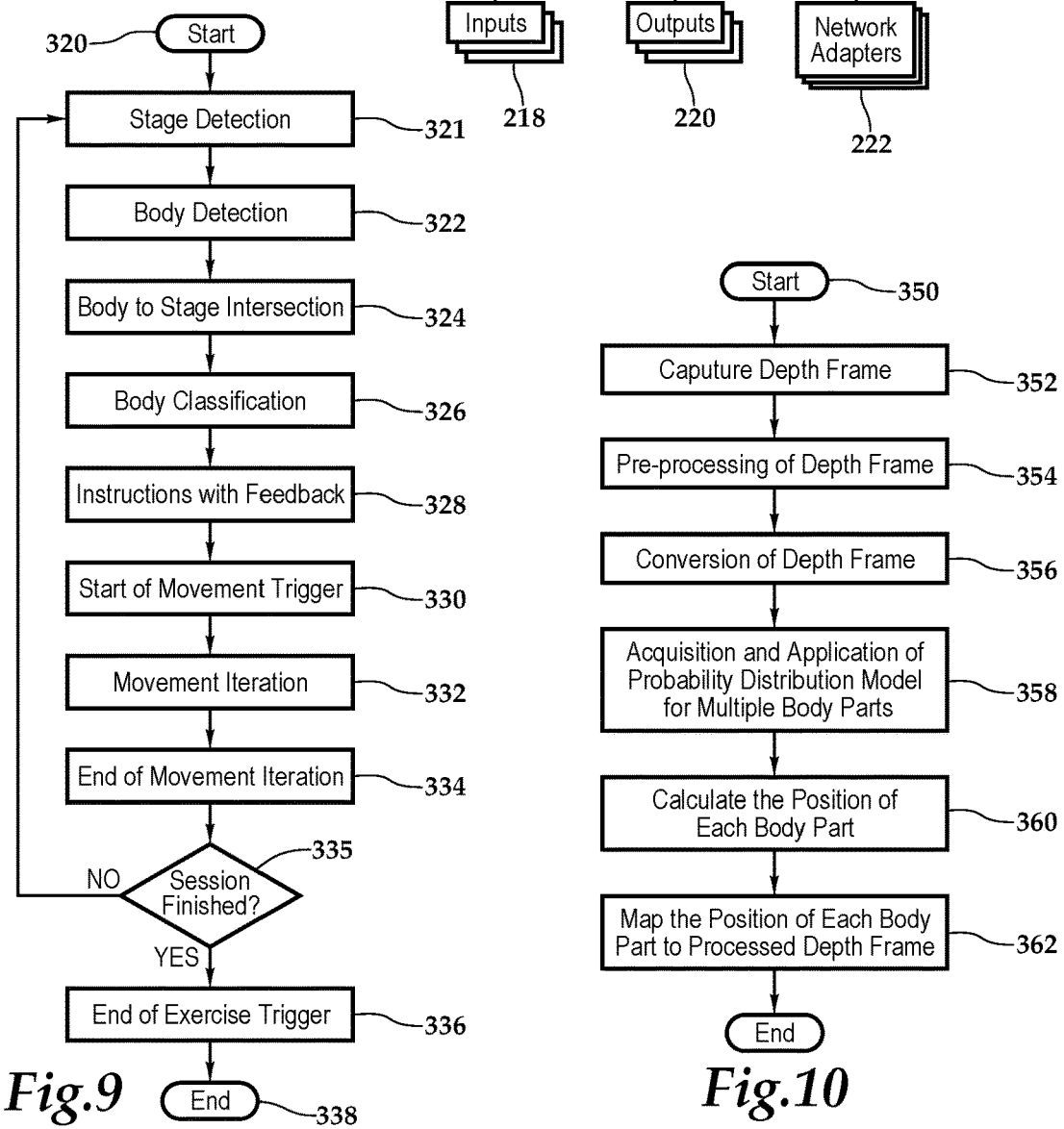
Fig.7
Fig.9
Fig.10

SYSTEM AND METHOD FOR HUMAN MOTION DETECTION AND TRACKING

PRIORITY STATEMENT & CROSS-REFERENCE TO RELATED APPLICATIONS

This application is a national entry under 35 U.S.C. § 371 of the International Application No. PCT/US2020/021262 entitled, "System and Method for Human Motion Detection and Tracking" filed on Mar. 5, 2020 in the name of Longbo Kong; which claims priority from U.S. Patent Application No. 62/814,147, entitled "System and Method for Human Motion Detection and Tracking" filed on Mar. 5, 2019, in the name of Longbo Kong; both of which are hereby incorporated by reference, in entirety, for all purposes.

TECHNICAL FIELD OF THE INVENTION

The present disclosure relates, in general, to biomechanical evaluations and assessments, which are commonly referred to as range of motion assessments, and more particularly, to automating a biomechanical evaluation process, including a range of motion assessment, and providing recommended exercises to improve physiological inefficiencies of a user.

BACKGROUND OF THE INVENTION

Human beings have regularly undergone physical examinations by professionals to assess and diagnose their health issues. Healthcare history has been predominantly reactive to an adverse disease, injury, condition or symptom. Increasingly, in modern times, with more access to information, a preventative approach to healthcare has been gaining greater acceptance. Musculoskeletal health overwhelmingly represents the largest health care cost. Generally speaking, a musculoskeletal system of a person may include a system of muscles, tendons and ligaments, bones and joints, and associated tissues that move the body and help maintain the physical structure and form. Health of a person's musculoskeletal system may be defined as the absence of disease or illness within all of the parts of this system. When pain arises in the muscles, bones, or other tissues, it may be a result of either a sudden incident (e.g., acute pain) or an ongoing condition (e.g., chronic pain). A healthy musculoskeletal system of a person is crucial to health in other body systems, and for overall happiness and quality of life. Musculoskeletal analysis, or the ability to move within certain ranges (e.g., joint movement) freely and with no pain, is therefore receiving greater attention. However, musculoskeletal analysis has historically been a subjective science, open to interpretation of the healthcare professional or the person seeking care.

In 1995, after years of research, two movement specialists, Gray Cook and Lee Burton, attempted to improve communication and develop a tool to improve objectivity and increase collaboration efforts in the evaluation of musculoskeletal health. Their system, the Functional Movement Screen (FMS), is a series of seven (7) different movement types, measured and graded on a scale of 0-3. While their approach did find some success in bringing about a more unified approach to movement assessments, the subjectivity, time restraint and reliance on a trained and accredited professional to perform the evaluation limited its adoption. Accordingly, there is a need for improved systems and methods for measuring and analyzing physiological deficiency of a person and providing corrective recommended exercises while minimizing the subjectivity during a musculoskeletal analysis.

SUMMARY OF THE INVENTION

It would be advantageous to achieve systems and methods that would improve upon existing limitations in functionality with respect to measuring and analyzing physiological deficiency of a person. It would also be desirable to enable a computer-based electronics and software solution that would provide enhanced goniometry serving as a basis for furnishing corrective recommended exercises while minimizing the subjectivity during a musculoskeletal analysis. To better address one or more of these concerns, a system and method for human motion detection and tracking are disclosed. In one embodiment, an optical sensing instrument monitors a stage. A memory is accessible to a processor and communicatively coupled to the optical sensing instrument. The system captures a depth frame from the optical sensing instrument. The depth frame may include at each image element first coordinate values including a point related to a distance from the optical sensing instrument. The depth frame is converted into a designated depth frame format, which includes at each image element second coordinate values relative to the depth frame. Acquired probability distribution models are applied to the designated depth frame format to identify body parts. In one embodiment, the system acquires probability distribution models for the designated depth frame format to identify the body parts, where the probability distribution models are generated by a neural network trained with markerless, colorless synthetic depth frames. In another embodiment, the system acquires probability distribution models for the designated depth frame format to linearly identify a respective plurality of body parts with the probability distribution models being single source generated by a neural network trained with markerless, colorless synthetic depth frames. The position of each of the body parts in the designated depth frame is calculated as is the position of each of the plurality of body parts in the depth frame. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 6 is a functional block diagram depicting one embodiment of the integrated goniometry system presented in FIGS. 2A and 2B;

FIG. 7 is a functional block diagram depicting one embodiment of a server presented in FIGS. 2A and 2B;

FIG. 9 is a flow chart depicting one embodiment of a method for integrated goniometric analysis according to exemplary aspects of the teachings presented herein;

FIG. 10 is a flow chart depicting one embodiment of a method for human motion detection and tracking according to the teachings presented herein;

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1A:
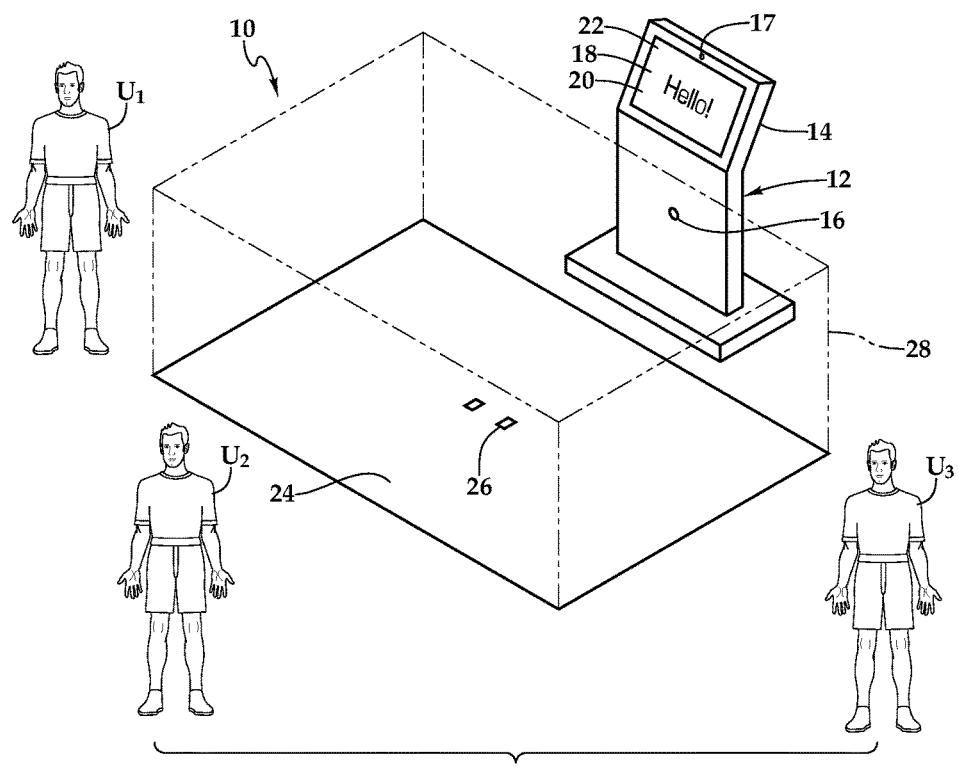
FIG. 1A is a schematic diagram depicting one embodiment of a system and method for human motion detection tracking for use, for example, with an integrated goniometry system for measuring and analyzing physiological deficiency of a person, such as a user, and providing corrective recommended exercises according to an exemplary aspect of the teachings presented herein.

Referring initially to FIG. 1A, therein is depicted one embodiment of a system for human motion detection and tracking that may be incorporated into an integrated goniometry system, for example, for performing automated biomechanical movement assessments, which is schematically illustrated and designated 10. As shown, the system 10 includes an integrated goniometer 12 having a housing 14 securing an optical sensing instrument 16 and a display 18. The display 18 includes an interactive portal 20 which provides prompts, such as a welcoming prompt 22, which may greet a crowd of potential users $U_1$, $U_2$, and $U_3$ and invite a user to enter a stage 24, which may include markers 26 for foot placement of a user standing at the markers 26 to utilize the integrated goniometry system 10. The stage 24 may be a virtual volumetric area 28, such as a rectangular or cubic area, that is compatible with human exercise positions and movement. The display 18 faces the stage 24 and the optical sensing instrument 16 monitors the stage 24. A webcam 17 may be included in some embodiments. It should be appreciated that the location of the optical sensing instrument 16 and the webcam 17 may vary with the housing 14. Moreover, the number of optical sensing instruments used may vary also. Multiple optical sensing instruments or an array thereof may be employed. It should be appreciated that the design and presentation of the integrated goniometer 12 may vary depending on application. By way of example, the integrated goniometer 12 and the housing 14 may be a device selected from the group consisting of smart devices, smart phones (with or without tripods), smart watches, smart wearables, stationary kiosks, wall mounted kiosks, and mobile kiosks, for example.

Figure 1B:
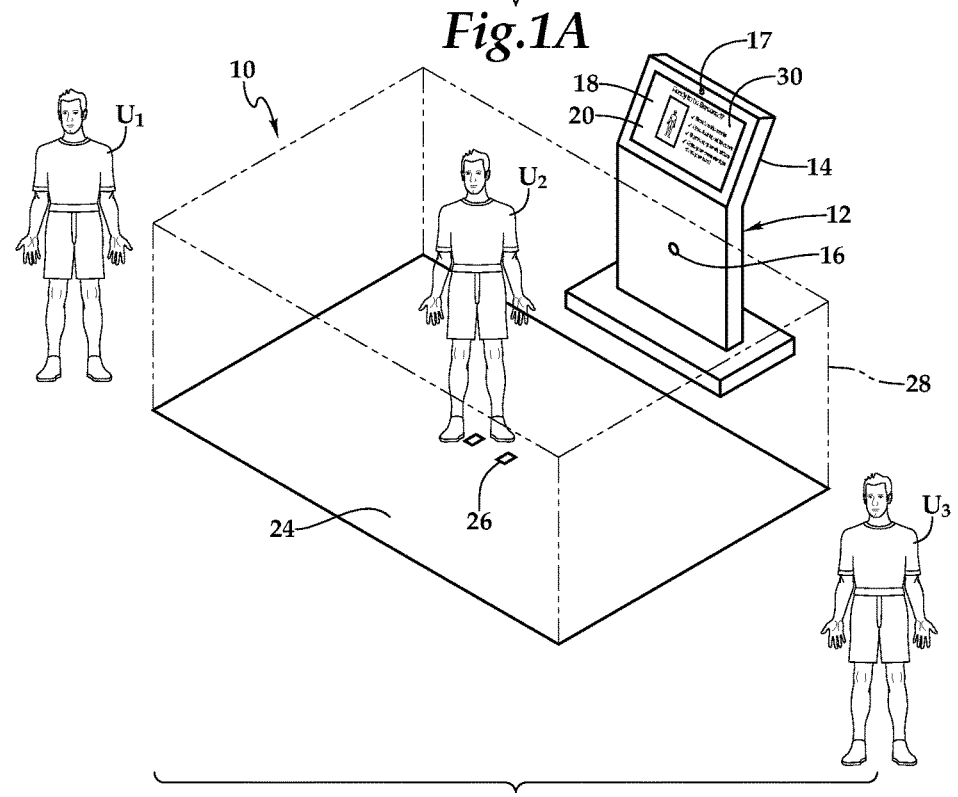
FIG. 1B is a schematic diagram depicting one embodiment of the system illustrated in FIG. 1A, wherein a user from a crowd has approached the system.

Referring now to FIG. 1B, a user, user $U_2$, has entered the stage 24 and the interactive portal 20 includes an exercise movement prompt 30 providing instructions for the user $U_2$ on the stage 24 to execute a set number of repetitions of an exercise movement, such as a squat or a bodyweight overhead squat, for example. A series of prompts on the interactive portal 20 instruct the user $U_2$ while the optical sensing instrument 16 senses body point data of the user $U_2$ during each exercise movement. Based on the sensed body point data, a mobility score, an activation score, a posture score, a symmetry score, or any combination thereof, for example, may be calculated. A composite score may also be calculated. One or more of the calculated scores may provide the basis for the integrated goniometry system 10 determining an exercise recommendation. As mentioned, a series of prompts on the interactive portal 20 instruct the user $U_2$ through repetitions of exercise movements while the optical sensing instrument 16 senses body point data of the user $U_2$.

Figure 2A:
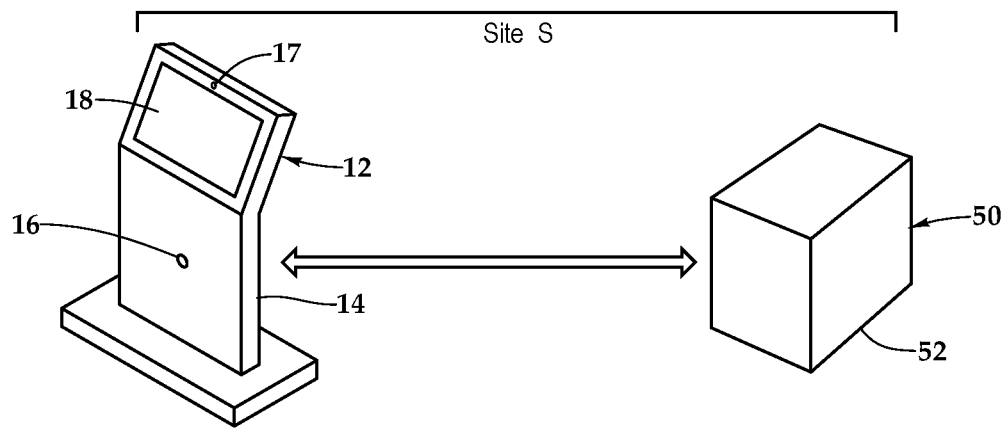
FIG. 2A is a schematic diagram depicting one embodiment of the system of FIG. 1 within an on-property deployment.

Referring now to FIG. 2A, a server 50, which supports the integrated goniometer 12 as part of the integrated goniometry system 10, may be co-located with the integrated goniometer 12, incorporated therewith within the housing 14, or remotely located to serve multiple integrated goniometers at different sites. The server 50, which includes a housing 52, is co-located on the site S with the integrated goniometer 12. It should be appreciated that the server 50 may be physically incorporated within the housing 52 as well. The server 50 provides various storage and support functionality to the integrated goniometer 12.

Figure 2B:
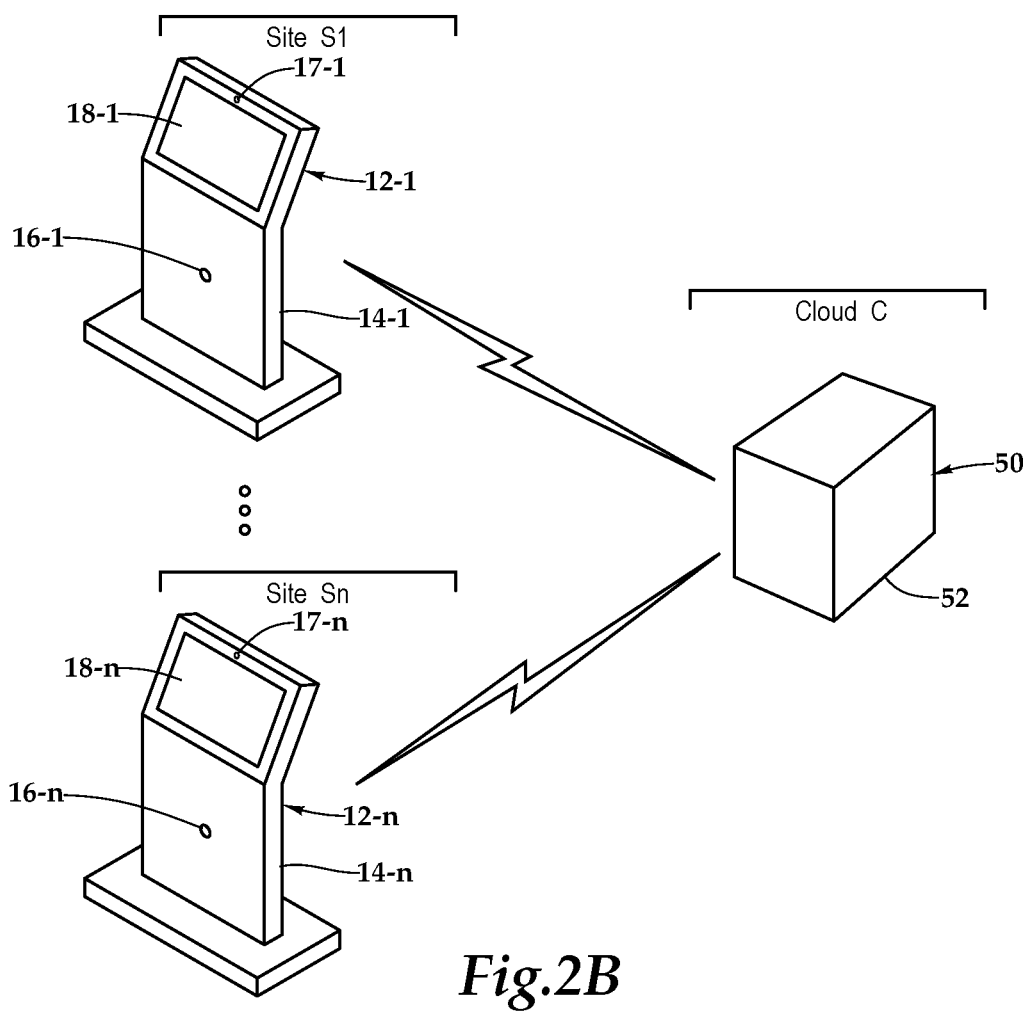
FIG. 2B is a schematic diagram depicting one embodiment of the system of FIG. 1 within a cloud-based computing deployment serving multiple sites.

Referring now to FIG. 2B, the integrated goniometry system 10 may be deployed such that the server 50 is remotely located in the cloud C to service multiple sites Si Sn with each site having an integrated goniometer 12-1 . . . 12-n and corresponding housings 14-1 . . . 14-n, optical sensing instruments 16-1 . . . 16-n, web cameras 17-1 . . . 17-n, and displays 18-1 . . . 18-n. The server 50 provides various storage and support functionality to the integrated goniometer 12.

Figure 3A:
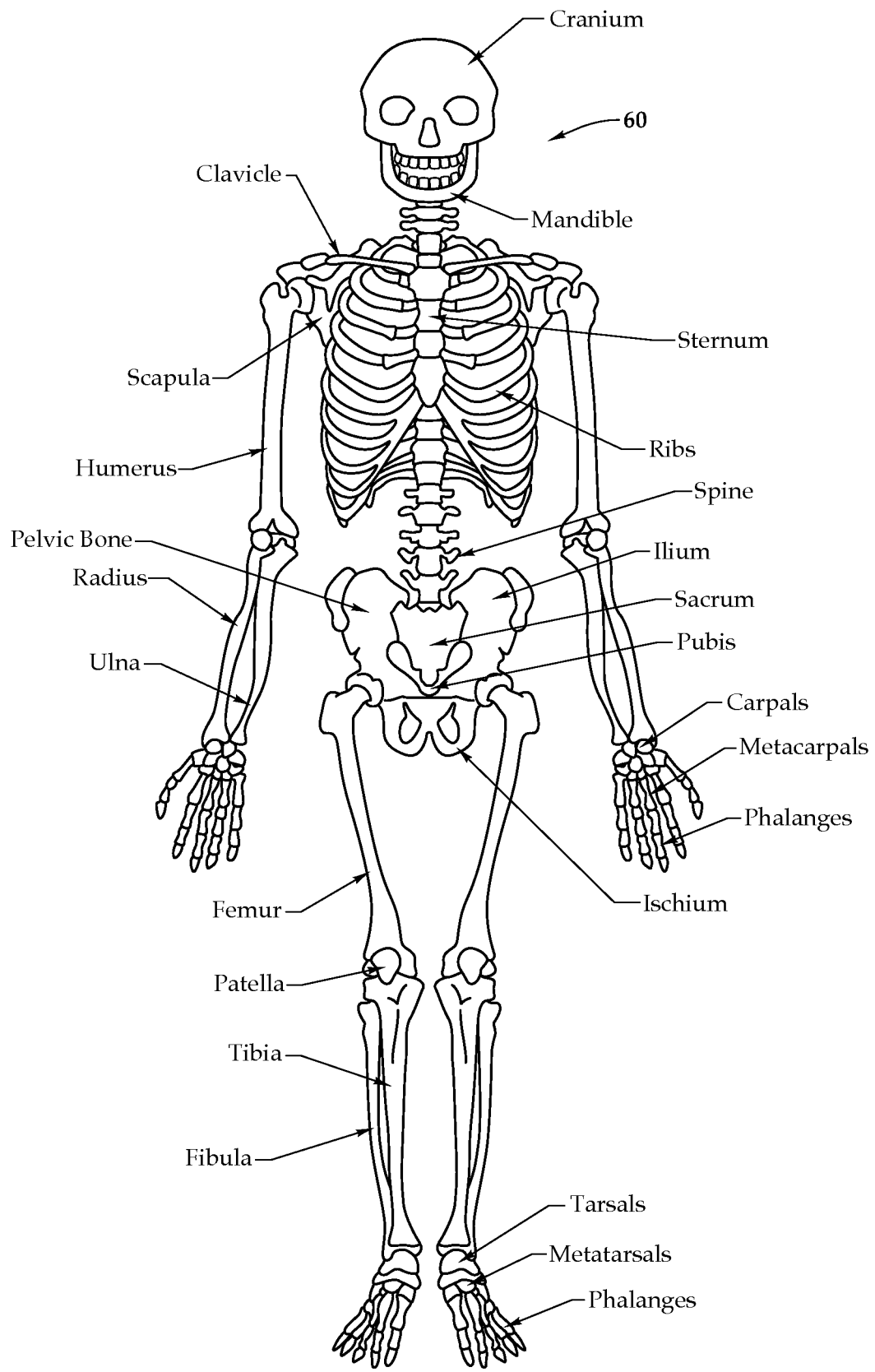
FIG. 3A is an illustration of a human skeleton.
Figure 3B:
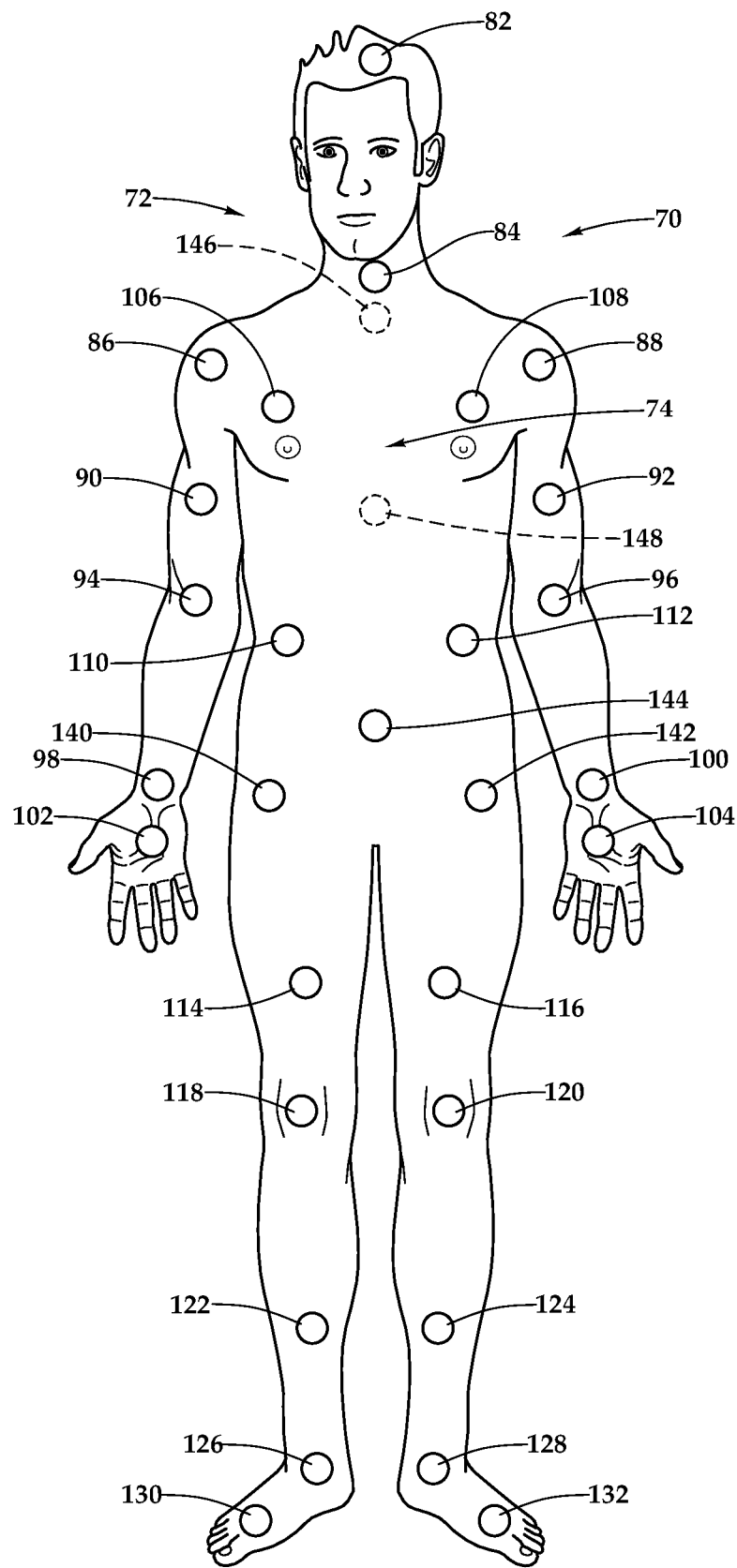
FIG. 3B is an illustration of one embodiment of body parts identified by the system.

Referring now to FIG. 3A and FIG. 3B, respective embodiments of a human skeleton 60 and body parts identified by the system 10 are depicted. Body part data 70 approximates certain locations and movements of the human body, represented by the human skeleton 60. More specifically, the body part data 70 is captured by the optical sensing instrument 16 and may include designated body part data 72 and synthetic body part data 74. By way of example and not by way of limitation, designated body part data 72 may include head data 82, neck data 84, right shoulder data 86, left shoulder data 88, right upper arm data 90, left upper arm data 92, right elbow data 94, left elbow data 96, right lower arm data 98, left lower arm data 100, right hand data 102, left hand data 104, right upper torso data 106, left upper torso data 108, right lower torso data 110, left lower torso data 112, upper right leg data 114, upper left leg data 116, right knee data 118, left knee data 120, right lower leg data 122, left lower leg data 124, right ankle data 126, left ankle data 128, right foot data 130, and left foot data 132. By way of example and not by way of limitation, synthetic body part data 74 may include right hip 140, left hip 142, waist 144, top of spine 146, and middle of spine 148. As will be appreciated, the synthetic body part data 74 may include data captured by the optical sensing instrument 16 that includes locations in the body in the rear of the person or data acquired through inference.

Figure 4:
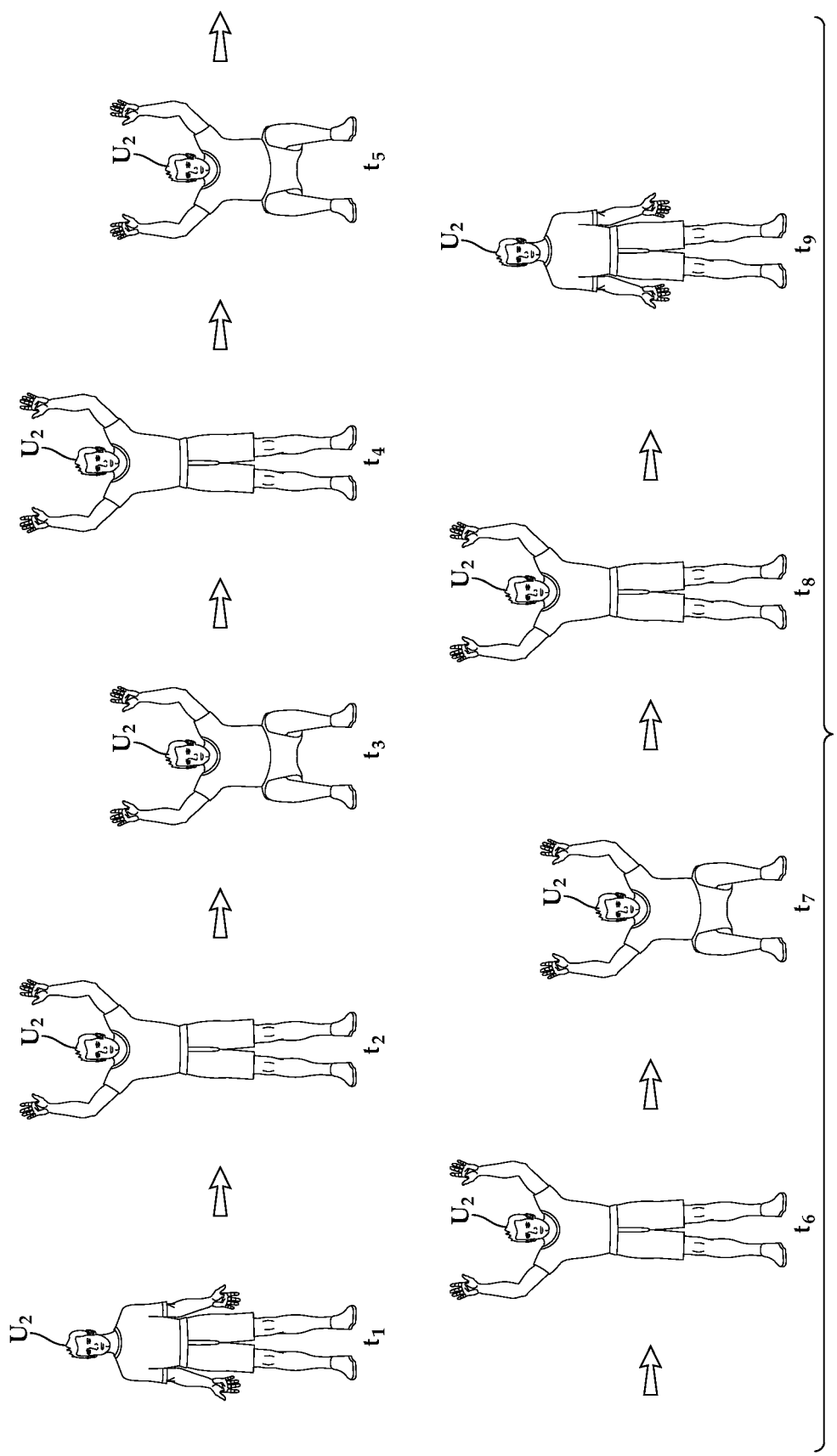
FIG. 4 is a diagram depicting one embodiment of a set number of repetitions which are monitored and captured by the system.

Referring now to FIG. 4, depth frames associated with a set number of repetitions of an exercise movement by the user $U_2$ are monitored and captured by the integrated goniometry system 10. As shown, in the illustrated embodiment, the user $U_2$ executes three squats and specifically three bodyweight overhead squats at $t_3$, $t_5$, and $t_7$. It should be understood, however, that a different number of repetitions may be utilized and is within the teachings presented herein. That is, N iterations of movement is provided for by the teachings presented herein. At $t_1$ and $t_9$, user $U_2$ is at a neutral position, which may be detected by sensing the body point data within the virtual volumetric area 28 of the stage 24 or at $t_9$, an exercise end position which is sensed with the torso in an upright position superposed above the left leg and the right leg with the left arm and right arm laterally offset to the torso.

At $t_2$, $t_4$, $t_6$, and $t_8$, the user $U_2$ is at an exercise start position. The exercise start position may be detected by the torso in an upright position superposed above the left leg and the right leg with the left arm and the right arm superposed above the torso. From an exercise start position, the user $U_2$ begins a squat with an exercise trigger. During the squat or other exercise movement, depth frames are collected. The exercise trigger may be displacement of the user from the exercise start position by sensing displacement of the body. Each repetition of the exercise movement, such as a squat, may be detected by sensing the body returning to its position corresponding to the exercise start position. By way of example, the spine midpoint may be monitored to determine to mark the completion of exercise movement repetitions.

Figure 5:
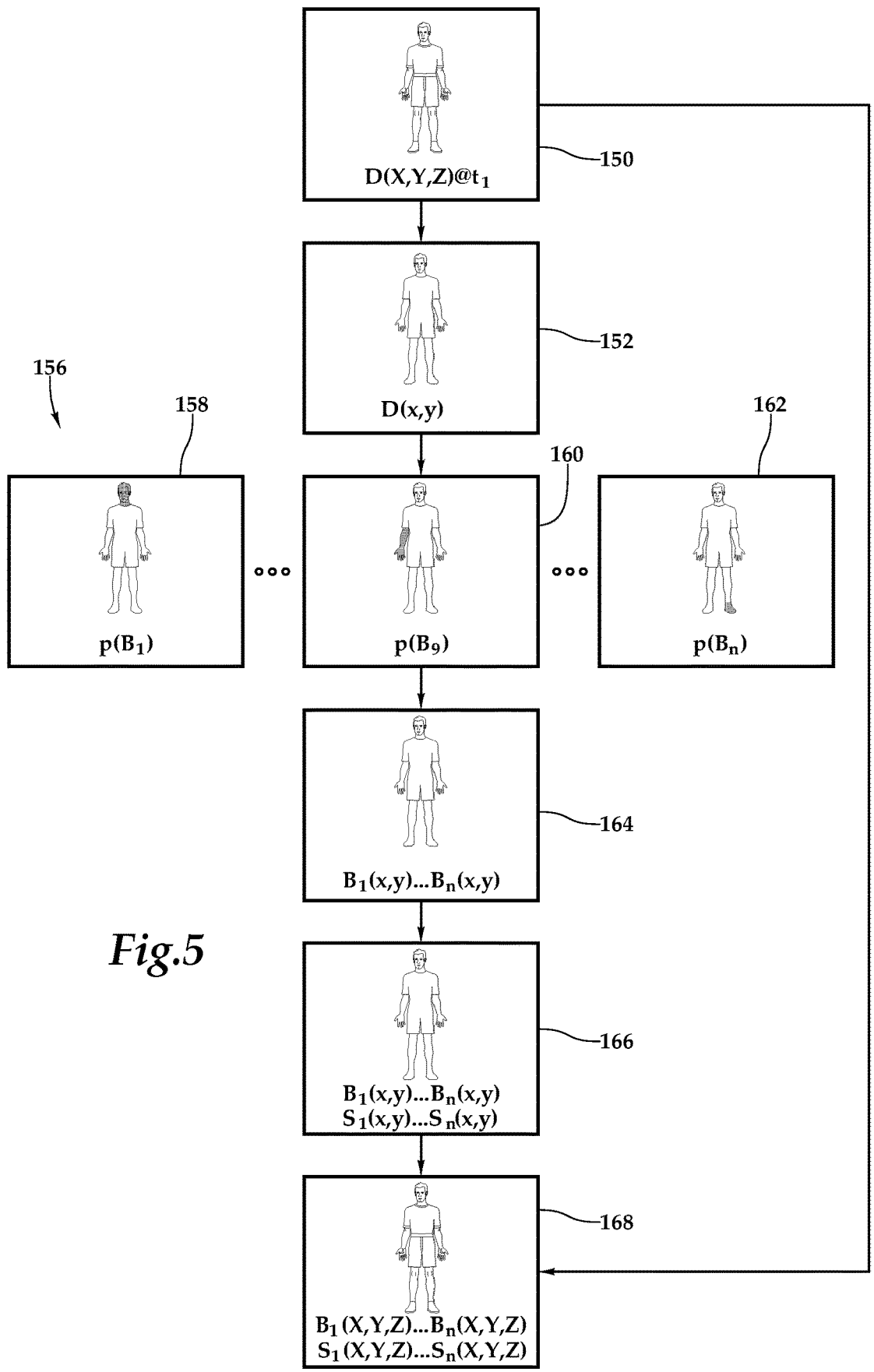
FIG. 5 is a diagram depicting one embodiment of a depth frame processing by the system.

Referring to FIG. 5, a depth frame 150 is captured having data at a time ti. The depth frame includes at each image element coordinate values D(X,Y,Z) including a point related to a distance from the optical sensing instrument 16. Pre-processing occurs to the depth frame 150 to provide a designated depth frame format 152. More particularly, the depth frame 150 is converted into a designated depth frame format 152 such that at each image element coordinate values D(x,y) are present relative to the depth frame 150. Also, during the pre-processing, the object is isolated. Next, as shown by element 156, probability distribution models are applied to the designated depth frame format 152 to identify body parts as shown by elements 158, 160, 162, which provide body part isolation. The position of each of the body parts in the designated depth frame is calculated as shown at depth frames 164, 166, 168 such that a composite depth frame is produced at the depth frame 164, a mapped depth frame is produced which isolates the subject at the depth frame 166, and the result is the depth frame 168 with a projection back to the full resolution. The position of each of the body parts in the depth frame is calculated with respect to the depth frame.

Referring to FIG. 6, within the housing 14 of the integrated goniometer 12, a processor 180, memory 182, and storage 184 are interconnected by a bus architecture 186 within a mounting architecture that also interconnects a network interface 188, a depth camera input 190, inputs 192, outputs 194, and the display 18. The processor 180 may process instructions for execution within the integrated goniometer 12 as a computing device, including instructions stored in the memory 182 or in storage 184. The memory 182 stores information within the computing device. In one implementation, the memory 182 is a volatile memory unit or units. In another implementation, the memory 182 is a non-volatile memory unit or units. Storage 184 provides capacity that is capable of providing mass storage for the integrated goniometer 12. The network interface 188 may provide a point of interconnection, either wired or wireless, between the integrated goniometer 12 and a private or public network, such as the Internet. Various inputs 192 and outputs 194 provide connections to and from the computing device, wherein the inputs 192 are the signals or data received by the integrated goniometer 12, and the outputs 194 are the signals or data sent from the integrated goniometer 12. The display 18 may be an electronic device for the visual presentation of data and may, as shown in FIG. 6, be an input/output display providing touchscreen control. The depth camera input 190 may provide an input to the optical sensing instrument 16, which may be a camera, a point-cloud camera, a laser-scanning camera, an infrared sensor, an RGB camera, or a depth camera, for example. By way of further example, the optical sensing instrument 16 may utilize technology such as time of flight, structured light, or stereo technology. By way of still further example, in instances where the optical sensing instrument 16 is a depth camera, a structured light camera, a time of flight camera, a passive stereo camera, or a combination thereof may be employed. Further, it should be appreciated that the optical sensing instrument 16 may include two optical sensing instruments; that is, more than one sensing instrument may be employed. As mentioned, the integrated goniometer 12 and the housing 14 may be a device selected from the group consisting of smart devices, smart phones (with or without tripods), smart watches, smart wearables, stationary kiosks, wall mounted kiosks, and mobile kiosks, for example.

The memory 182 and storage 184 are accessible to the processor 180 and include processor-executable instructions that, when executed, cause the processor 180 to execute a series of operations. In a first series of operations, the processor-executable instructions cause the processor 180 to display an invitation prompt on the interactive portal. The invitation prompt provides an invitation to the user to enter the stage 24 prior to the processor-executable instructions causing the processor 180 to detect the user on the stage 24 by sensing body point data within the virtual volumetric area 28. By way of example and not by way of limitation, the body point data may include first torso point data, second torso point data, first left arm point data, second left arm point data, first right arm point data, second right arm point data, first left leg point data, second left leg point data, first right leg point data, and second right leg point data, for example.

The processor-executable instructions cause the processor 180 to display an exercise movement prompt on the interactive portal 20. The exercise movement prompt 30 provides instructions for the user to execute an exercise movement for a set number of repetitions with each repetition being complete when the user returns to an exercise start position. The processor 180 is caused by the processor-executable instructions to detect an exercise trigger. The exercise trigger may be displacement of the user from the exercise start position by sensing displacement of the related body point data. The processor-executable instructions also cause the processor 180 to display an exercise end prompt on the interactive portal 20. The exercise end prompt provides instructions for the user to stand in an exercise end position. Thereafter, the processor 180 is caused to detect the user standing in the exercise end position.

The processor-executable instructions cause the processor 180 to calculate one or more of several scores including calculating a mobility score by assessing angles using the body point data, calculating an activation score by assessing position within the body point data, calculating a posture score by assessing vertical differentials within the body point data, and calculating a symmetry score by assessing imbalances within the body point data. The processor-executable instructions may also cause the processor 180 to calculate a composite score based on one or more of the mobility score, the activation score, the posture score, or the symmetry score. The processor-executable instructions may also cause the processor 180 to determine an exercise recommendation based on one or more of the composite score, the mobility score, the activation score, the posture score, or the symmetry score.

In a second series of operations, the processor-executable instructions cause the processor 180 to capture a depth frame from the optical sensing instrument 16. The depth frame may include at each image element coordinate values including a point related to a distance from the optical sensing instrument 16. Then the processor 180 may be caused to convert the depth frame into a designated depth frame format 152. The designated depth frame format 152 may include at each image element, coordinate values relative to the depth frame. The processor executable instructions may cause the processor 180 to acquire and apply multiple probability distribution models to the designated depth frame format 152 to identify a respective plurality of body parts. In acquiring the multiple probability distribution models, the probability distribution models may be generated by a neural network trained with markerless, colorless synthetic depth frames. The markerless, colorless synthetic depth frames inform a system having real-time tracking with improved accuracy and rapid posting of results. In some implementations, the system acquires probability distribution models for the designated depth frame format 152 to linearly identify a respective plurality of body parts with the probability distribution models being single source generated by a neural network trained with markerless, colorless synthetic depth frames. Next, the processor 180 may be caused to calculate the position of each of the plurality of body parts in the designated depth frame and then calculate the position of each of the plurality of body parts in the depth frame.

Referring now to FIG. 7, one embodiment of the server 50 as a computing device includes, within the housing 52, a processor 210, memory 212, storage 214, interconnected with various buses 216 in a common or distributed, for example, mounting architecture, that also interconnects various inputs 218, various outputs 220, and network adapters 222. In other implementations, in the computing device, multiple processors and/or multiple buses may be used, as appropriate, along with multiple memories and types of memory. Further still, in other implementations, multiple computing devices may be provided and operations distributed therebetween. The processor 210 may process instructions for execution within the server 50, including instructions stored in the memory 212 or in storage 214. The memory 212 stores information within the server 50 as the computing device. In one implementation, the memory 212 is a volatile memory unit or units. In another implementation, the memory 212 is a non-volatile memory unit or units. Storage 214 includes capacity that is capable of providing mass storage for the server 50. Various inputs 218 and outputs 220 provide connections to and from the server 50, wherein the inputs 218 are the signals or data received by the server 50, and the outputs 220 are the signals or data sent from the server 50. The network adapters 222 connect the server 50 to a network shared by the integrated goniometer 12.

The memory 212 is accessible to the processor 210 and includes processor-executable instructions that, when executed, cause the processor 210 to execute a series of operations. In a first set of processor-executable instructions, the processor-executable instructions cause the processor 210 to update periodically or on-demand, depending on the operational configuration, a database which may be part of storage 214 of body point data, exercise recommendations, composite scores, mobility scores, activation scores, posture scores, and symmetry scores associated with various users. The processor-executable instructions cause the processor 210 to make this database or a portion thereof available to the integrated goniometer 12 by way of the integrated goniometer 12 receiving the information through fetching or the server 50 sending the requested information. Further, the processor-executable instructions cause the processor 210 to execute any of the processor-executable instructions presented in association with the integrated goniometer 12, for example.

In a second series of operations, the processor-executable instructions cause the processor 210 to capture a depth frame from the optical sensing instrument. The depth frame may include at each image element coordinate values including a point related to a distance from the optical sensing instrument. Then the processor 210 may be caused to convert the depth frame into a designated depth frame format 152. The designated depth frame format 152 may include at each image element, coordinate values relative to the depth frame. The processor executable instructions may cause the process to apply multiple probability distribution models to the designated depth frame format 152 to identify a respective plurality of body parts. The probability distribution models may be generated by a neural network trained with markerless, colorless synthetic depth frames. Next, the processor 210 may be caused to calculate the position of each of the body parts in the designated depth frame and then calculate the position of each of the body parts in the depth frame.

With respect to FIGS. 6 and 7, in some embodiments, the processor 180 and the memory 182 of the integrated goniometer 12 and the processor 210 and the memory 212 of the server 50 cooperate to execute processor-executable instructions in a distributed manner By way of example, in these embodiments, the server 50 may be a local server co-located with the integrated goniometer 12, or the server 50 may be located remotely to the integrated goniometer 12, or the server 50 may be a cloud-based server. In these embodiments, by way of example, the processor-executable instructions cause the processors 180, 210, in a distributed manner, to capture a depth frame from the optical sensing instrument 16. The depth frame may include at each image element coordinate values including a point related to a distance from the optical sensing instrument 16. Then the processors 180, 210, in a distributed manner, may be caused to convert the depth frame into a designated depth frame format 152. The designated depth frame format 152 may include at each image element, coordinate values relative to the depth frame. The processor executable instructions may cause the process to apply multiple probability distribution models to the designated depth frame format 152 to identify a respective plurality of body parts. The probability distribution models may be generated by a neural network trained with markerless, colorless synthetic depth frames. Next, the processors 180, 210, in a distributed manner, may be caused to calculate the position of each of the body parts in the designated depth frame and then calculate the position of each of the body parts in the depth frame.

Figure 8:
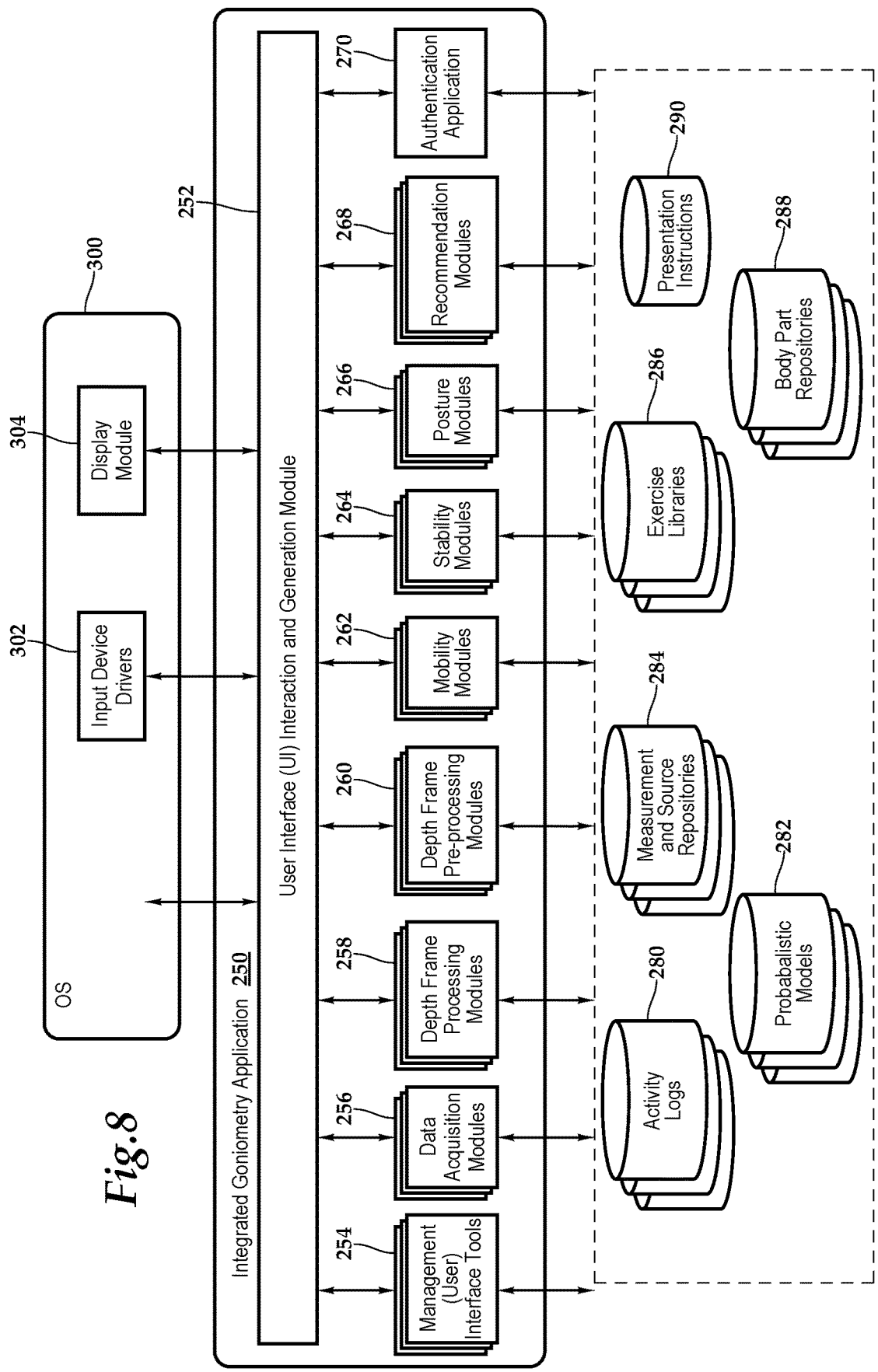
FIG. 8 is a conceptual module diagram depicting a software architecture of an integrated goniometry application of some embodiments.

FIG. 8 conceptually illustrates the software architecture of an integrated goniometry application 250 of some embodiments that may automate the biomechanical evaluation process and provide recommended exercises to improve physiological inefficiencies of a user. In some embodiments, the integrated goniometry application 250 is a stand-alone application or is integrated into another application, while in other embodiments the application might be implemented within an operating system 300. Furthermore, in some embodiments, the integrated goniometry application 250 is provided as part of a server-based solution or a cloud-based solution. In some such embodiments, the integrated goniometry application 250 is provided via a thin client. That is, the integrated goniometry application 250 runs on a server while a user interacts with the application via a separate machine remote from the server. In other such embodiments, integrated goniometry application 250 is provided via a thick client. That is, the integrated goniometry application 250 is distributed from the server to the client machine and runs on the client machine.

The integrated goniometry application 250 includes a user interface (UI) interaction and generation module 252, management (user) interface tools 254, data acquisition modules 256, depth frame processing modules 258, depth frame pre-processing modules 260, mobility modules 262, stability modules 264, posture modules 266, recommendation modules 268, and an authentication application 270. The integrated goniometry application 250 has access to activity logs 280, probabilistic models 282, measurement and source repositories 284, exercise libraries 286, body part repositories 228, and presentation instructions 290, which presents instructions for the operation of the integrated goniometry application 250 and particularly, for example, the aforementioned interactive portal 20 on the display 18. In some embodiments, storages 280, 282, 284, 286, 288, and 290 are all stored in one physical storage. In other embodiments, the storages 280, 282, 284, 286, 288, and 290 are in separate physical storages, or one of the storages is in one physical storage while the other is in a different physical storage.

The UI interaction and generation module 250 generates a user interface that allows, through the use of prompts, the user to quickly and efficiently perform a set of exercise movements to be monitored with the body point data collected from the monitoring furnishing an automated biomechanical movement assessment scoring and related recommended exercises to mitigate inefficiencies. Prior to the generation of automated biomechanical movement assessment scoring and related recommended exercises, the data acquisition modules 256 may be executed to obtain instances of the body point data via the optical sensing instrument 16, which is then processed with the assistance of the depth frame processing modules 258 and the depth frame pre-processing modules 260. Following the collection of the body point data, the mobility modules 262, stability modules 264, and the posture modules 266 are utilized to determine a mobility score, an activation score, and a posture score, for example. More specifically, in one embodiment, the mobility modules 262 measure a user's ability to freely move a joint without resistance. The stability modules 264 provide an indication of whether a joint or muscle group may be stable or unstable. The posture modules 266 may provide an indication of physiological stresses presented during a natural standing position. Following the assessments and calculations by the mobility modules 262, stability modules 264, and the posture modules 266, the recommendation modules 268 may provide a composite score based on the mobility score, the activation score, and the posture score as well as exercise recommendations for the user. The authentication application 270 enables a user to maintain an account, including an activity log and data, with interactions therewith.

In the illustrated embodiment, FIG. 8 also includes the operating system 300 that includes input device drivers 302 and a display module 304. In some embodiments, as illustrated, the input device drivers 302 and display module 304 are part of the operating system 300 even when the integrated goniometry application 250 is an application separate from the operating system 300. The input device drivers 302 may include drivers for translating signals from a keyboard, a touch screen, or an optical sensing instrument, for example. A user interacts with one or more of these input devices, which send signals to their corresponding device driver. The device driver then translates the signals into user input data that is provided to the UI interaction and generation module 252.

FIG. 9 depicts one embodiment of a method for integrated goniometric analysis. At block 320, the methodology begins with the integrated goniometer positioned facing the stage 24, with stage detection occurring at block 321. At block 322, multiple bodies are simultaneously detected by the integrated goniometer 12 in and around the stage 24. As the multiple bodies are detected, a prompt displayed on the interactive portal 20 of the integrated goniometer 12 invites one of the individuals to the area of the stage 24 in front of the integrated goniometer 12. At block 324, one of the multiple bodies is isolated by the integrated goniometer 12 and identified as an object of interest once it separates from the group of multiple bodies and enters the stage 24 in front of the integrated goniometer 12. At block 326, the identified body, a user, is tracked as a body of interest by the integrated goniometer 12.

At block 328, the user is prompted to position himself into the appropriate start position which will enable the collection of a baseline measurement and key movement measurements during exercise. At this point in the methodology, the user is prompted by the integrated goniometer 12 to perform the exercise start position and begin a set repetitions of an exercise movement. The integrated goniometer 12 collects body point data to record joint angles and positions. At block 330, the integrated goniometer 12 detects an exercise or movement trigger which is indicative of phase movement discrimination being performed in a manner that is independent of the body height, width, size or shape or the user.

At block 332, the user is prompted by the integrated goniometer 12 to repeat the exercise movement as repeated measurements provide more accurate and representative measurements. A repetition is complete when the body of the user returns to the exercise start position. The user is provided a prompt to indicate when the user has completed sufficient repetitions of the exercise movement. With each repetition, once in motion, monitoring of body movement will be interpreted to determine a maximum, minimum, and moving average for the direction of movement, range of motion, depth of movement, speed of movement, rate of change of movement, and change in the direction of movement, for example. At block 334, the repetitions of the exercise movement are complete. Continuing to decision block 335, if the session is complete, then methodology advances to block 336. If the session is not complete, then the methodology returns to the block 321. At block 336, once the required number of repetitions of the exercise movement are complete, the user is prompted to perform an exercise end position, which is a neutral pose. With the exercise movements complete, the integrated goniometry system 12 begins calculating results and providing the results and any exercise recommendations to the user.

Figure 11:
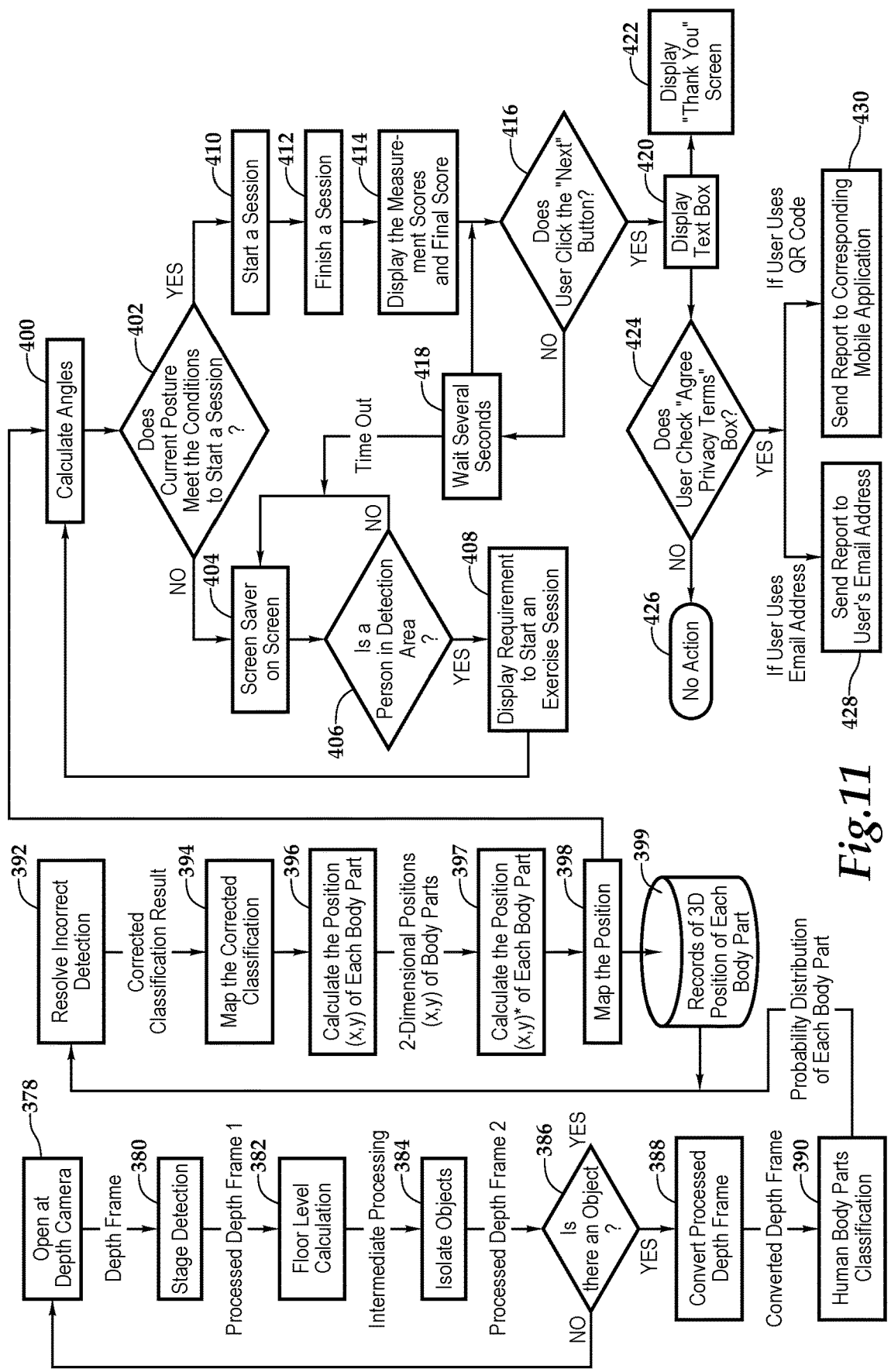
FIG. 11 is a flow chart depicting another embodiment of a method for human motion detection and tracking.

FIG. 10 and FIG. 11 show the methodology in more detail with elements 350 through 362 and elements 378 through 430. Referring now to FIG. 10, the methodology begins with block 350 and continues to block 352 where a depth frame is captured. The depth frame may be captured by the optical sensing instrument. By way of example and not by way of limitation, depth frame acquisition may involve obtaining raw depth frame data from a depth camera, obtaining raw 3D point cloud data from a depth camera, or obtaining raw color frame data from a color sensor build into a depth camera. At block 354, pre-processing of the depth frame occurs. As previously discussed, during pre-processing, the depth frame is converted into a designated depth frame format such that at each image element coordinate values D(x,y) are present relative to the depth frame. Also, during the pre-processing, the object may be isolated. At block 356, the depth frame is converted into the designated depth frame format before the acquisition and application of a probability distribution model or models occurs for the body parts. The probability distribution models may be generated by a neural network trained with markerless, colorless synthetic depth frames. With the use of markerless, colorless synthetic depth frames, the neural network provides a depth model that mitigates light conditions and therefore, to a degree, independent of lighting conditions. By mitigation the effects of light, the position of each of the body parts may be calculated more accurately at block 360 before the position of each body part is mapped at block 362.

Referring now to FIG. 11, the methodology is initiated with the operation of the depth camera at block 378 capturing a depth frame and the methodology detecting the stage 380 and initiating a processing of the depth frame. During the processing steps represented by the blocks 378, 380, target area locationing occurs, which may include locating a 3D target area in terms of width, height, and length for a user to perform certain activities with the data collected by depth camera or other optical sensing instrument. At block 382, a floor level calculation occurs and an intermediate processing of the depth frame occurs. More particularly, within the target area, floor estimation and removal occurs, which includes calculating the approximate floor level and removing the corresponding floor area data from the data. At block 384, an object, such as a user or body part of the user, is isolated within the depth frame. After successful removal of the floor area, detection and separation of objects, including objects separate from the user, occurs and these objects are removed from the data. At decision block 386, if an object is located within the depth frame then the process continues to block 388. On the other hand, if an object is not located within the depth frame then the process returns to the operation of the depth camera at block 378.

At block 388, with the object located within the depth frame, the processed depth frame is converted to a converted depth frame having the desired designated depth frame format. At block 390, the object or objects within the depth frame are classified to determine the human body parts and a probability distribution for each body part is provided. At block 392, any incorrect detections resulting from the classification at the block 390 are resolved to furnish a corrected classification result with the classification results being mapped at block 394. At block 396, the position of each body part is calculated to provide the two-dimensional positions of the body parts. At block 397, the position of each body part within a 3D model is then calculated and mapped (block 398) and recorded (block 399). As shown, the records of the 3D position of each body part at block 399 are provided as an input into block 392 to assist in the resolution of an incorrect detection. Additionally, as shown, following block 398, at block 400 various angles are calculated.

At the blocks 388 through 400, neural networks are employed to identify body parts on the detected object, i.e., the human. In some embodiments, probability distribution models are acquired and applied to the designated depth frame format to identify the body parts, with the probability distribution models being generated by a neural network trained with markerless, colorless synthetic depth frames. Additionally, any ambiguous and incorrect results from the neural network are resolved. The 2D(x,y) positions for each of the body parts on the depth frame are calculated and then mapped to 3D space (X,Y,Z) and output as 3D position of each body part. In one implementation, the positions (X,Y,Z) in 3D space are represented in millimeter units. Positions of the body parts in 2D are represented in pixel unit and the value of each position may vary depending on different resolutions of the depth sensor.

At decision block 402, if the current posture as determined by the calculation of angles at block 400 meets conditions, then a session starts at block 410. On the other hand, if the calculation of angles at block 400 indicates that a session should not be started, then the process progresses to block 404, where a screen saver is provided. At decision block 406, if a person is not in the detection area, then the process returns to block 404. If, however, a person is in the detection area, then at block 408 instructions are provided to the person on how to start an exercise session before the process returns to block 400. With respect to the block 400 and the decision block 402, it should be appreciated that the methodology presented herein, and the related system, provide an autonomous user interface with hands-free human-machine interaction. Based on the outputs, the methodology determines whether or not a user is performing a required activity. The methodology also ensures a user is provided with the necessary guidance.

Returning to the decision block 402, if the current posture meets the conditions to start a session, then the methodology advances to block 410, where a session is started and then finished at block 412. Then, at block 414, measurement scores and final scores are displayed. At decision block 416, if the user indicates a willingness to progress, then the process continues to block 420. Otherwise, the process continues to block 418, where a timeout occurs if sufficient time lapses. Returning to block 420, information is displayed in a box before the process continues to a "thank you" notification at block 422 and a user is presented with an opportunity to receive a report at decision block 424. If the user has not agreed to the terms shown, then no action is taken at block 426; otherwise, via email (block 428) or application (block 430), for example, the report is shared with the user.

Figure 12:
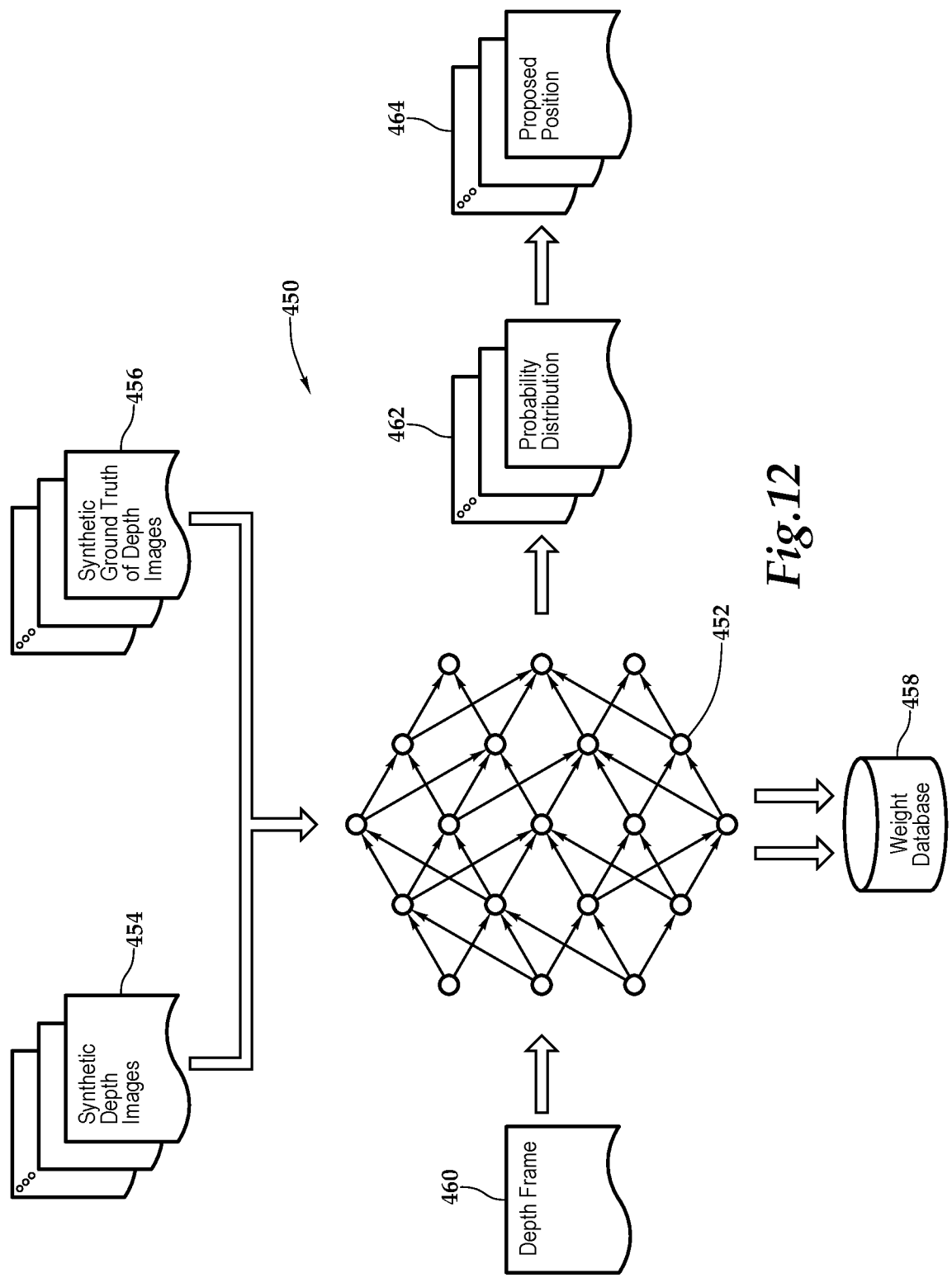
FIG. 12 is a schematic diagram depicting one embodiment of a neural network according to the teachings presented herein.

FIG. 12 depicts one embodiment of a neural network training and deployment subsystem 450. As shown, a neural network 452 is trained by synthetic depth images 454 and synthetic ground truth of depth images 456. The synthetic depth images 454 provide training data sets to the neural network 454, with, for example, domain randomization on a large set of synthetic depth images that simulate the data of real depth images. In one implementation, the synthetic depth images 454 include markerless, colorless synthetic depth frames. The synthetic ground truth of depth images 456 provides the desired reality that the neural network 452, once trained, predicts to ensure accuracy. Learning in the neural network 452 involves adjusting the weights and optional thresholds of the neural network 452 to improve the accuracy of the results and this data is stored in a weight database 458.

As shown, in one operational embodiment of the neural network training and deployment subsystem 450, a depth frame 460 is provided as an input to the neural network 452, which outputs a probability distribution 462 for each body part prior, which in turn, provides a proposed position (x,y) 464 for each body part. In this way the integrated goniometry system 10 acquires multiple probability distribution models using the neural network training and deployment subsystem 450 to the designated depth frame format to identify a respective number of body parts. As mentioned, the probability distribution models are generated by the neural network 452 trained with markerless, colorless synthetic depth frames. Moreover, as shown, the neural network training and deployment subsystem 450 acquires probability distribution models for the designated depth frame format to linearly identify respective body parts with the probability distribution models being single source generated by the neural network 452 trained with markerless, colorless synthetic depth frames. The single source generation from one neural network provides a linear application of the probability distribution models. Therefore, the linear application of the probability distribution models occurs directly and without the need to resolve conflicts between the probability distribution models and without the need to use combinatory practices, voting practices, or additional performance resources, which may be required in instances of more than one neural network source or in instances of non-linear application models.

With the use of markerless, colorless synthetic depth frames, the neural network 452 provides a depth model that mitigates light conditions and therefore, to a degree, independent of lighting conditions. The use of the markerless, colorless synthetic depth frames contributes to faster and more accurate human motion detection and tracking. Additionally, the use of the markerless, coloroless synthetic depth frames ensures a sufficiently large sample size that is inherently consistent, without human labeling errors. Further, the use of the markerless, coloroless synthetic depth frames ensures privacy while maintaining flexibility in a dataset that is free of human-introduced labeling errors.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A system for human motion detection and tracking, the system comprising:
a housing securing an optical sensing instrument, a display, a processor, and memory therewith;
a busing architecture communicatively interconnecting the optical sensing instrument, the display, the processor, and the memory;
the optical sensing instrument monitoring a stage, the stage being a virtual volumetric area that is compatible with human exercise positions and movement, the stage including a volume in space at a monitoring distance from the optical sensing instrument; and
the memory accessible to the processor, the memory including processor-executable instructions that, when executed, cause the processor to:
capture a depth frame from the optical sensing instrument, the depth frame including at each image element first coordinate values including a point related to a distance from the optical sensing instrument,
convert the depth frame into a designated depth frame format, the designated depth frame format including at each image element second coordinate values relative to the depth frame,
acquire a plurality of probability distribution models for the designated depth frame format to linearly identify a respective plurality of body parts, the plurality of probability distribution models being single source generated by a neural network trained with markerless, colorless synthetic depth frames,
calculate a position of each of the respective plurality of body parts in the designated depth frame format, and
calculate the position of each of the respective plurality of body parts in the depth frame.

2. The system as recited in claim 1, wherein the optical sensing instrument further comprises an instrument selected from the group consisting of a camera, a point-cloud camera, a laser-scanning camera, an infrared sensor, and an RGB camera.

3. The system as recited in claim 1, wherein the optical sensing instrument further comprises a technology selected from the group consisting of time of flight, structured light, and stereo technology.

4. The system as recited in claim 1, wherein the optical sensing instrument further comprises a depth camera.

5. The system as recited in claim 4, wherein the depth camera further comprises a camera selected from the group consisting of a structured light camera, a time of flight camera, a passive stereo camera, and combinations thereof.

6. The system as recited in claim 1, wherein the optical sensing instrument further comprises a plurality of depth cameras.

7. The system as recited in claim 1, wherein the housing further comprises a display communicatively interconnected with the busing architecture.

8. The system as recited in claim 7, wherein the display faces the stage, the display including an interactive portal.

9. A system for human motion detection and tracking, the system comprising:
  a housing securing an optical sensing instrument, a processor, and memory therewith;
  a busing architecture communicatively interconnecting the optical sensing instrument, the processor, and the memory; and
  the memory accessible to the processor, the memory including processor-executable instructions that, when executed, cause the processor to:
    convert a depth frame into a designated depth frame format, the designated depth frame format including at each image element second coordinate values relative to the depth frame,
    acquire a plurality of probability distribution models for the designated depth frame format to linearly identify a respective plurality of body parts, the plurality of probability distribution models being single source generated by a neural network trained with markerless, colorless synthetic depth frames,
    calculate a position of each of the respective plurality of body parts in the designated depth frame format, and
    calculate the position of each of the respective plurality of body parts in the depth frame.

10. A system for human motion detection and tracking, the system comprising:
  an integrated goniometer comprising:
    a housing securing an optical sensing instrument, a processor, and memory therewith;
    a busing architecture communicatively interconnecting the optical sensing instrument, the processor, and the memory;
    the optical sensing instrument monitoring a stage, the stage being a virtual volumetric area that is compatible with human exercise positions and movement, the stage including a volume in space at a monitoring distance from the optical sensing instrument;
  a server comprising:
    a server housing securing a server processor, and a server memory therewith, and
    a server busing architecture communicatively interconnecting the server processor and the server memory;
  a data link providing communication between the integrated goniometer and the server; and
  the memory accessible to the processor and the server memory accessible to the server processor, processor-executable instructions distributed between the memory and the server memory that, when executed, cause the processor and the server processor, in a distributed manner via the data link, to:
  capture a depth frame from the optical sensing instrument, the depth frame including at each image element first coordinate values including a point related to a distance from the optical sensing instrument,
  convert the depth frame into a designated depth frame format, the designated depth frame format including at each image element second coordinate values relative to the depth frame,
  acquire a plurality of probability distribution models for the designated depth frame format to linearly identify a respective plurality of body parts, the plurality of probability distribution models being single source generated by a neural network trained with markerless, colorless synthetic depth frames,
  calculate a position of each of the respective plurality of body parts in the designated depth frame, and
  calculate the position of each of the respective plurality of body parts in the depth frame.

* * * * *